(12) United States Patent
Pagan

(10) Patent No.: US 7,363,925 B2
(45) Date of Patent: Apr. 29, 2008

(54) GAS-TREATMENT DEVICES

(75) Inventor: Eric Pagan, Hythe (GB)

(73) Assignee: Smiths Group PLC, London (GB)

(*) Notice: Subject to any disclaimer, the term of this patent is extended or adjusted under 35 U.S.C. 154(b) by 335 days.

(21) Appl. No.: 11/001,124

(22) Filed: Dec. 2, 2004

(65) Prior Publication Data

US 2005/0133028 A1 Jun. 23, 2005

(30) Foreign Application Priority Data

Dec. 18, 2003 (GB) ................ 0329297.6

(51) Int. Cl.
*A61B 11/00* (2006.01)
(52) U.S. Cl. ............... 128/200.24; 128/207.14; 128/207.15
(58) Field of Classification Search ........ 128/200.26, 128/201.13, 204.17, 205.12, 207.14, 207.15, 128/207.29, 200.24; 623/9
See application file for complete search history.

(56) References Cited

U.S. PATENT DOCUMENTS 3,548,823 A * 12/1970 Bogacik ............. 128/205.29
3,881,482 A * 5/1975 Lindholm ............ 128/201.13
4,829,997 A * 5/1989 Douwens et al. ...... 128/201.13
5,042,468 A * 8/1991 Lambert ............. 128/200.26
5,195,527 A * 3/1993 Hicks ................ 128/205.12
5,201,309 A * 4/1993 Friberg et al. ......... 128/207.14
5,617,913 A * 4/1997 DeGregoria et al. ... 165/104.11
5,840,091 A * 11/1998 Strong ................ 55/385.1
6,422,235 B1 7/2002 Persson
6,634,354 B2 * 10/2003 Christopher .......... 128/200.26
6,769,430 B1 * 8/2004 Carlsen et al. ........ 128/201.13

FOREIGN PATENT DOCUMENTS

GB 2 338 195 12/1999

* cited by examiner

*Primary Examiner*—Steven O. Douglas
(74) *Attorney, Agent, or Firm*—Louis Woo

(57) ABSTRACT

An HME for a tracheostomy tube has a flexible outer housing of a gas-permeable material containing an HME element of discrete particles, granules or the like of a hygroscopic material. The particles are contained between the outer housing and an inner wall of a foam. The inner wall has a ciliated surface facing the end of the tube, which acts to distribute gas over the surface of the HME element. The HME is attached to a flange on an inner cannula by means of a removable adhesive. The HME may include a suction port through a self-closing aperture, which makes a wiping seal with a suction catheter inserted in the tube.

26 Claims, 1 Drawing Sheet

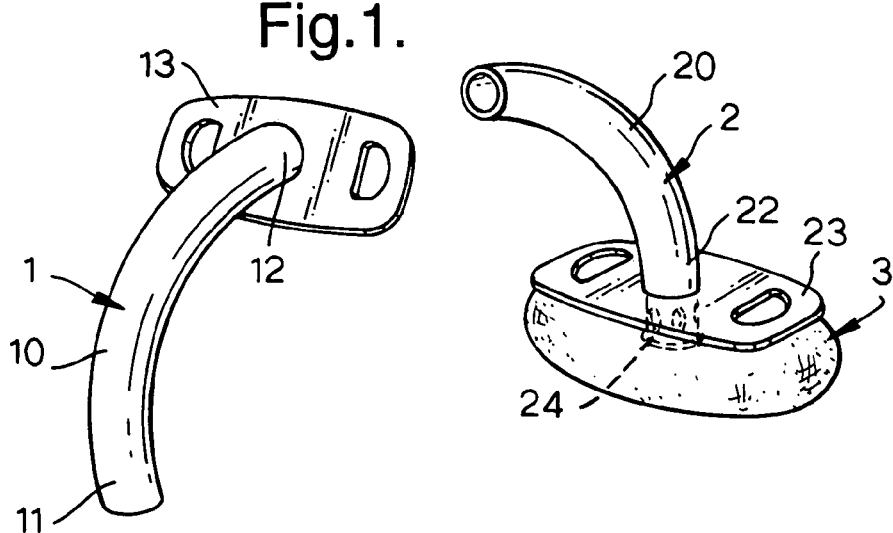
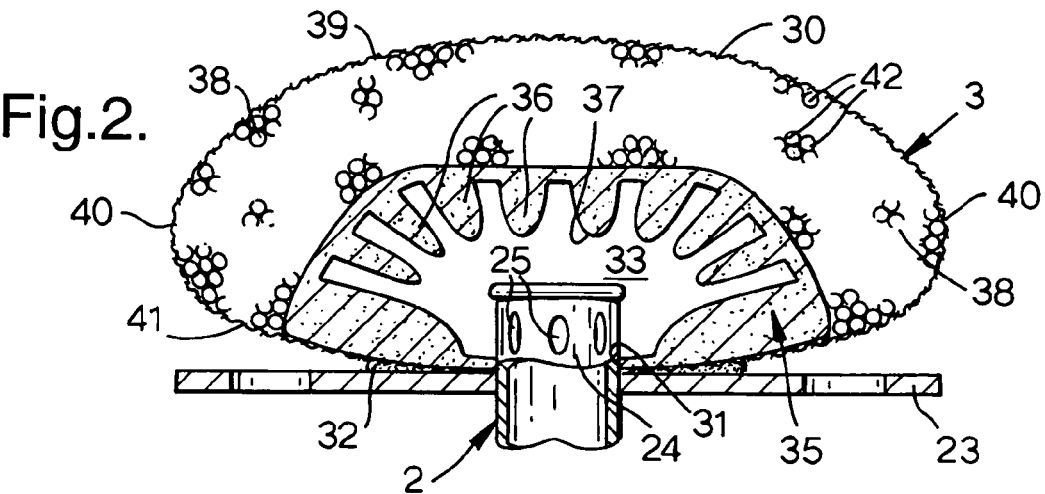
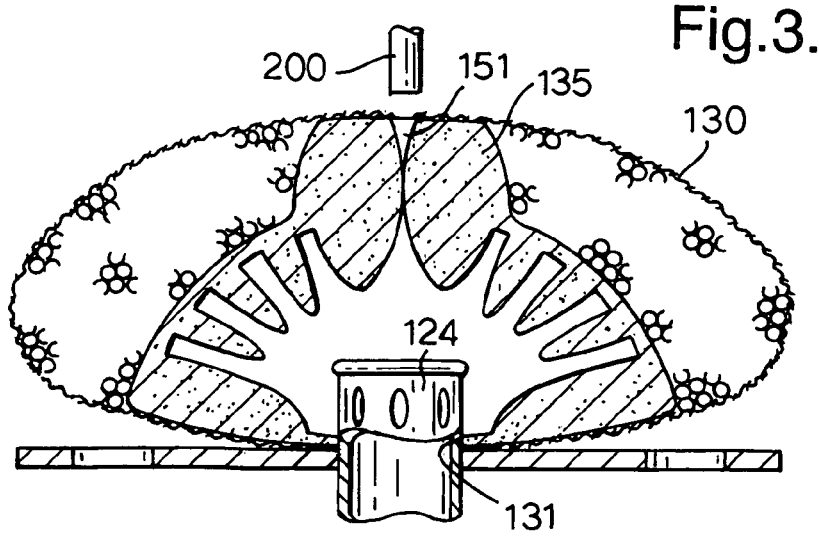

GAS-TREATMENT DEVICES

BACKGROUND OF THE INVENTION

This invention relates to gas-treatment devices.

The invention is more particularly concerned with heat and moisture exchangers (HMEs) or the like for use with tracheostomy tubes.

In normal breathing, inhaled air passes through the nose where it is warmed and moistened before passing to the trachea and bronchial passages. Where a patient breathes via a tracheal tube or laryngeal mask, gas is supplied directly to the trachea, by-passing the nose. The gas is, therefore, preferably warmed and moistened to prevent discomfort and damage to the lining of the trachea. This is often achieved by a heat and moisture exchange device or HME connected to the tracheal tube to receive both exhaled and inhaled gases. The HME has a moisture-absorbing element, such as of a treated paper or foam, that absorbs moisture in exhaled gases and transfers a major part of this to the inhaled gases. The element also warms inhaled gas in the same way. HMEs are sold by Portex Limited of Hythe, England under the trade mark Thermovent. Examples of HMEs are described in: GB 2303307; GB 2321600; GB 2277689; GB 2268496; GB2267840; GB 2233904; EP 535016; EP 533644; EP 387220; EP 265163; EP 413127; U.S. Pat. No. 4,516,573; U.S. Pat. No. 4,090,513; U.S. Pat. No. 4,771,770; U.S. Pat. No. 4,200,094; and U.S. Pat. No. 4,048,993. The HME may also include a filter for removing particles, bacteria and viruses from gas supplied to or from the patient.

Conventional HMEs have an exchange element within a rigid housing that is coupled to the machine end of the tracheal tube. This can be relatively bulky and is a particular problem where the patient is breathing unaided via a tracheostomy tube since it is preferable for this to be as unobtrusive as possible.

BRIEF SUMMARY OF THE INVENTION

It is an object of the present invention to provide an alternative gas-treatment device and assembly.

According to one aspect of the present invention there is provided a gas-treatment device for connection to the machine end of a patient breathing tube, the device being conformable.

The device preferably includes a flexible outer housing and a gas-treatment element that is substantially conformable to the shape of the outer housing. The outer housing is preferably of a gas-permeable material, such as a fabric. The device preferably includes an HME element. The HME element may include a discrete material, such as in the form of particles, granules or small balls. The HME element may include a zeolite. The device may include a flexible outer housing, a conformable gas-treatment element within the housing and gas-dispersion means within the housing arranged to disperse gas over the gas-treatment element. The gas-dispersion means may include a ciliated surface. The patient breathing tube is preferably a tracheostomy tube. The gas-treatment device may be supported on a flange of the tube and is preferably removably attached with the flange, such as by means of an adhesive. The breathing tube preferably has a coupling extending within the gas-treatment device, the coupling having at least one side port. The gas-treatment device may include a self-sealing port arranged to be aligned with the machine end of the breathing tube such as to enable an elongate member to be inserted through the port and the device, into the tube. The port is preferably arranged to make a wiping seal with the elongate member.

According to another aspect of the present invention there is provided a gas-treatment device including a port for connection to a patient breathing tube and a gas-treatment element, the device including an outer wall of gas-permeable material such that gas passes to and from the patient breathing tube via the port, the gas-treatment element and through the outer wall.

The wall may be of a fabric and the gas-treatment element may be an HME element. The HME element may include a discrete material, such as in the form of particles, granules or small balls.

According to a further aspect of the present invention there is provided an assembly of a breathing tube and a gas-treatment device according to the above one or other aspect of the invention.

The breathing tube preferably includes an outer tube and a removable inner cannula inserted within the outer tube, the gas-treatment device being mounted at the machine end of the inner cannula.

A tracheostomy tube assembly including an HME, in accordance with the present invention, will now be described, by way of example, with reference to the accompanying drawing.

BRIEF DESCRIPTION OF THE DRAWING

FIG. 1 is a perspective view of the assembly;

FIG. 2 is a partly cross-sectional view of a part of the assembly showing the HME; and FIG. 3 is a partly cross-sectional view of a part of an alternative assembly having a modified HME.

DETAILED DESCRIPTION OF THE PREFERRED EMBODIMENT

With reference first to FIGS. 1 and 2, the assembly comprises an outer, tracheostomy tube 1, a removable inner cannula or liner 2 and an HME gas-treatment device 3 connected to the machine end of the cannula. When inserted, the inner cannula 2 is considered to form a part of the tracheostomy tube 1.

The tracheostomy tube 1 is conventional having a shaft 10 curved to the anatomy of the patient so that, in use, its patient end 11 is directed caudally within the trachea. The machine end 12 of the tube 1 terminates flush with a laterally-extending flange 13 shaped to lie flat on the patient's skin to either side of the tracheostomy.

The cannula 2 has a shaft 20 curved to the same shape as the tracheostomy tube 1 and its external diameter is such that it is a close sliding fit within the tracheostomy tube. The cannula 2 also has a flange 23 at its machine end 22 of the same shape as the flange 13 of the tracheostomy tube so that the two flanges lie close to one another when assembled. A short cylindrical coupling 24 projects from the rear, machine side of the flange 23. The coupling 24 has a tapered female bore adapted to receive a 15 mm male coupling and it also has a number of side ports 25 equally spaced around its circumference. The side ports 25 are arranged so that they will be occluded when a male coupling or 15 mm connector is inserted.

The HME 3 is fitted over the coupling 24 and is attached to the flange 23. The HME 3 has an outer wall or housing 30 of a bonded-fibre fabric or other gas-permeable flexible material, such as a perforated material. The housing 30 has a generally rectangular shape, when viewed along the axis of the cannula 2, that follows approximately the outline of the flange 23. Alternatively, the housing could be oval or elliptical viewed along the axis of the cannula. In section, as shown in FIG. 2, the housing 30 is oval. Centrally in one side of the housing 30 there is a circular aperture 31 the diameter of which is approximately equal to the external diameter of the coupling 24. A region 32 on the outside of the housing 30 around the aperture 31 has a low-tack adhesive, which forms a secure, gas-tight seal with the machine side of the flange 23. The HME could be attached to the cannula in other ways, such as by a mechanical clasp or by hook-and-loop fabric. The coupling 24 projects through the aperture 31 into a central cavity 33 within the housing 30. The cavity 33 is enclosed by a porous foam sponge wall or insert 35 having multiple fingers 36 projecting inwardly towards the aperture 31 to provide a ciliated surface 37 to the cavity.

The HME 3 is completed by an HME element 38 located between the wall 30 and the foam insert 35. The element 38 extends along the machine-end face 39 of the housing 30 and the edges 40 but not along the major part of the patient-end face 41 in the region 32 because contact with the flange 23 in this region prevents passage of gas. The HME element 38 is of a discrete material, that is, it is formed of separate discrete pieces so that it can conform freely to the shape of the housing 30. In particular, the element 38 is formed from particles 42 of zeolites, which act as molecular sieves, or small balls of foam or paper treated with a hygroscopic material of the kind commonly used in HME paper elements.

The HME 3, therefore, has a soft, conformable nature of the same kind as a bean bag and can be laid substantially flat over the machine side of the flange 23.

In use, the cannula 2 is inserted in the tracheostomy tube 1 of a patient who is breathing spontaneously. The two flanges 13 and 23 are secured together to hold the cannula 2 in position. When the patient exhales, air flows along the bore of the inner cannula 2, through the coupling 24, via its open end and the side ports 25, into the cavity 33 within the HME 3. The fingers 36 of the sponge element 35 distribute the air over the entire surface of the HME element 38 for maximum efficiency so that the major part of the heat and moisture in the exhaled breath is transferred to the element. The foam member 35 also takes some part in absorbing the heat and moisture. The gas then flows out through the wall 30 of the HME 3 over a relatively large area. When the patient inhales, air flows in through the wall 30, through the element 38 and the foam 35 taking up the major part of the heat and moisture absorbed in these parts. The warmed and moistened air then flows through the coupling 24 along the tracheostomy tube 1, via the inner cannula 2, to the patient.

The arrangement of the present invention enables a low profile HME to be provided, which is inconspicuous, does not interfere with bedding and clothing and produces less leverage on the tube to which it is connected. The HME presents a conformable external surface, which also makes it comfortable where it comes into contact with the skin. The porous nature of the wall acts as a coarse filter preventing inhalation of larger particles and insects etc. Because the air flows in and out over a large area there is a reduced risk of occlusion.

The inner cannula with the HME is removed and replaced periodically when secretions start to collect. It will be appreciated, however, that the HME could be attached directly to the flange of the tracheostomy tube where an inner cannula is not used, the HME being removed and replaced as necessary. If access is needed to the coupling 24, such as to connect the patient to a ventilator or resuscitator, the HME can be readily removed by pulling apart the adhesive join at the region 32.

The HME could be modified to allow use of a suction catheter, endoscope or other elongate member, as shown in FIG. 3 where similar components have been given the same reference number with the addition of 100. The housing 130 is of a similar shape to the housing 30 shown in FIG. 2 but it has a second aperture 151 located directly opposite the aperture 131 in which the coupling 124 is received. The second aperture 151 differs from the first in that it is normally closed, being formed by a passage through the foam member 135, which is extended to the wall 130 around the aperture. The aperture 151 is closed resiliently by the nature of the foam but can be opened when it is necessary to insert a suction catheter 200 or the like along the tracheostomy tube simply by pushing the catheter through the aperture. The foam member 135 around the aperture 151 contacts the catheter 200 around its circumference to provide a wiping seal that restricts the escape of gas through the aperture around the outside of the catheter.

The invention, in some of its aspects, is not confined to HMEs but could be used with other gas-treatment devices such as filters.

What I claim is:

1. A gas-treatment device comprising an externally-closed housing having an inner surface that defines a shape, a gas-treatment element and an inlet for connection to a machine end of a patient breathing tube, wherein said gas-treatment element is substantially entirely enclosed by said housing and wherein both of said housing and said gas-treatment element are flexible and porous, such that said device is conformable and said gas-treatment element contacts and conforms to the shape and size of substantially the entire inner surface of said housing, and such that substantially all gas flow to said patient breathing tube through is through the thickness of the wall of the housing and through the gas-treatment element.

2. A gas-treatment device according to claim 1, wherein said housing is of a fabric.

3. A gas-treatment device according to claim 1, wherein said gas-treatment element is an HME element.

4. A gas-treatment device according to claim 3, wherein said HME element includes a discrete material.

5. A gas-treatment device according to claim 4, wherein said discrete material is in the form of particles, granules or small balls.

6. A gas-treatment device according to claim 3, wherein said HME element includes a zeolite.

7. A gas-treatment device according to claim 1, wherein said housing contains a gas-disperser arranged to disperse gas over said gas-treatment element.

8. A gas-treatment device according to claim 7, wherein said gas-disperser includes a ciliated surface.

9. A gas-treatment device according to claim 1, wherein said patient breathing tube is a tracheostomy tube.

10. A gas-treatment device according to claim 1, wherein said tube has a flange at its machine end, and wherein said gas-treatment device is supported on said flange.

11. A gas-treatment device according to claim 10, wherein said gas-treatment device is removably attached with said flange.

12. A gas-treatment device according to claim 10, wherein said gas-treatment device is attached with said flange by means of an adhesive.

13. A gas-treatment device according to claim 1, wherein said breathing tube has a coupling extending within said gas-treatment device, and wherein said coupling has at least one side port.

14. A gas-treatment device according to claim 1, including a self-sealing port arranged to be aligned with a machine end of said breathing tube such as to enable an elongate member to be inserted through said port and said device, into said tube.

15. A gas-treatment device according to claim 14, wherein said port is arranged to make a wiping seal with said elongate member.

16. A gas-treatment device comprising an outer, closed wall of a gas-permeable material having an inner surface that defines a shape, a gas-treatment element substantially entirely enclosed within said outer wall and conforms to the shape and size of the entire inner surface of said outer wall, and a port for connection to a patient breathing tube such that substantially all gas passes to and from said patient breathing tube via said port, said gas-treatment element and through the thickness of said outer wall.

17. A gas-treatment device according to claim 16, wherein said wall is of a fabric.

18. A gas-treatment device according to claim 16, wherein said gas-treatment element is an HME element.

19. A gas-treatment device according to claim 18, wherein said HME element includes a discrete material.

20. A gas-treatment device according to claim 19, wherein said discrete material is in the form of particles, granules or small balls.

21. An assembly comprising a breathing tube and a gas-treatment device according to claim 1, wherein said breathing tube includes an outer tube and a removable inner cannula inserted within said outer tube, and wherein said gas-treatment device is mounted at a machine end of said inner cannula.

22. An HME comprising: an outer flexible, closed wall of gas-permeable material; an inner porous wall within the outer flexible wall; said walls having respective inner surfaces; an HME element of a discrete material between said outer and inner walls that contacts and conforms to the shape and size of the respective inner surfaces of said walls and is substantially entirely enclosed between said walls; a inner cavity divided from said HME element by said porous wall; and an opening into said cavity by which gas can be supplied to and from said cavity and through the thickness of said inner wall, through said HME element and said outer wall.

23. An assembly comprising: a breathing tube having a patient end and a machine end; a gas-treatment device comprising an outer, closed flexible wall of a flexible gas-permeable material, said wall having an inner surface that defines a shape a gas-treatment element substantially entirely enclosed within and contacts and conforms to the shape and size of substantially the entire inner surface of said outer wall, and a port connected to a patient breathing tube such that substantially all gas passes to and from said patient breathing tube via said port, said gas-treatment element and through the thickness of said outer wall.

24. An assembly according to claim 23, wherein said gas-treatment device is an HME.

25. An assembly comprising: a breathing tube having a patient end and a machine end; a flange at said machine end; and a gas-treatment device according to claim 1 mounted on said flange and presenting a conformable external surface.

26. An assembly according to claim 25, wherein said gas-treatment device is an HME.

* * * * *